Figure 1:
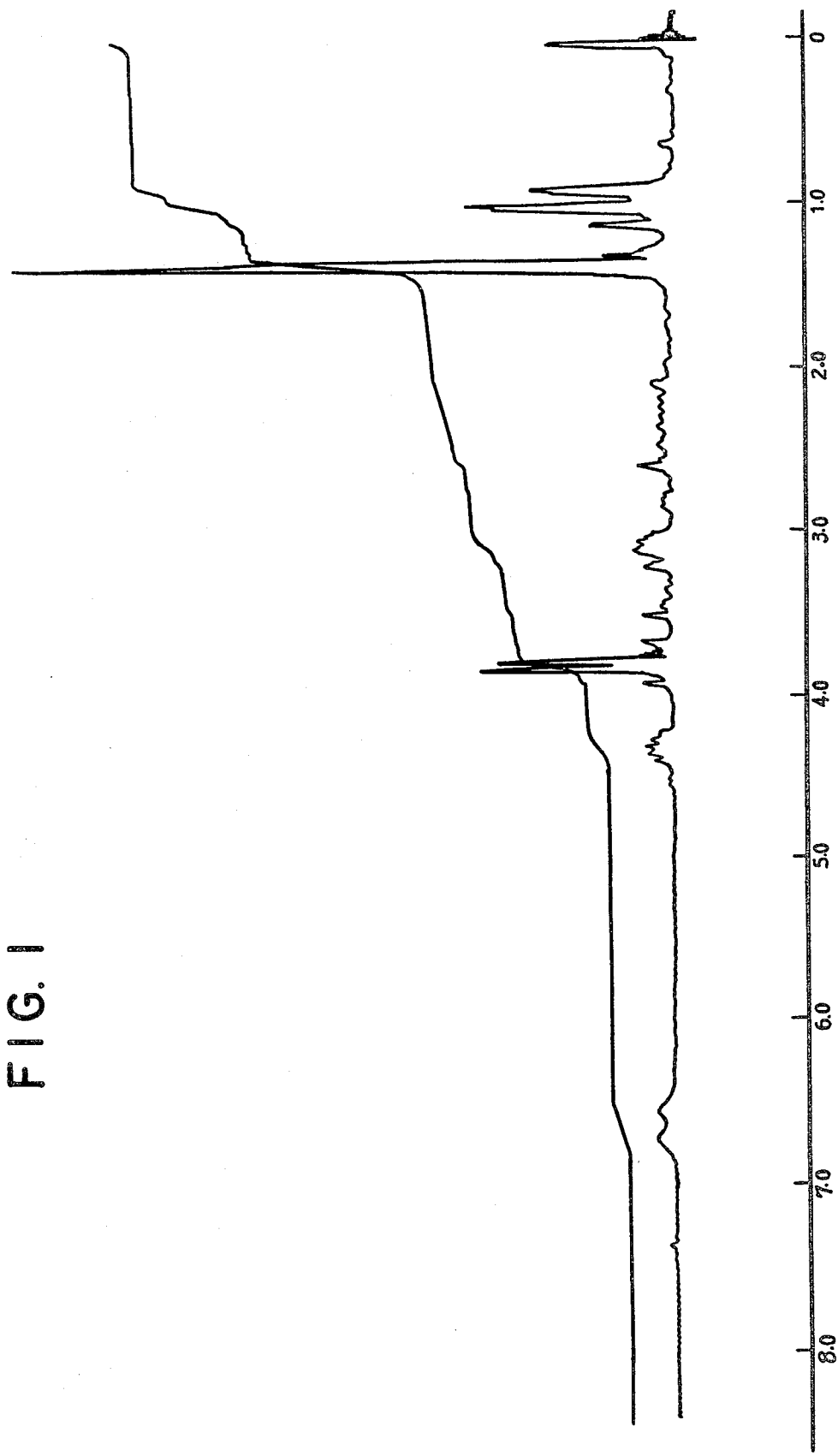

United States Patent [19]

Hirata et al.

[11] 4,322,345
[45] Mar. 30, 1982

[54] 2-AZETIDINONE 4-CARBOXY DERIVATIVES AND A PROCESS FOR PRODUCING THE SAME

[75] Inventors: Tadashi Hirata, Yokohama; Akira Sato; Nobuhiro Nakamizo, both of Machida, all of Japan

[73] Assignee: Kyowa Hakko Kogyo Kabushiki Kaisha, Tokyo, Japan

[21] Appl. No.: 142,542

[22] Filed: Apr. 21, 1980

Related U.S. Application Data

[63] Continuation of Ser. No. 947,223, Sep. 29, 1978, abandoned.

[30] Foreign Application Priority Data

Sep. 30, 1977 [JP] Japan .................................. 52/118120
Feb. 23, 1978 [JP] Japan .................................. 53/20010
Mar. 3, 1978 [JP] Japan .................................. 53/24150
Sep. 2, 1978 [JP] Japan .................................. 53/13791

[51] Int. Cl.$^3$ ................. C07D 205/08; C07D 31/395; C07D 403/06
[52] U.S. Cl. ............................. 260/239 A; 260/245.4; 260/340.9 R; 260/346.73; 260/347.3; 260/347.4; 424/244; 424/246; 424/271; 542/400; 542/469; 542/470
[58] Field of Search ............ 260/239 A, 245.4, 347.3, 260/347.4, 346.73; 532/400, 469, 470

[56] References Cited

U.S. PATENT DOCUMENTS 4,181,800 1/1980 Kamiya et al. ...................... 545/180

FOREIGN PATENT DOCUMENTS 1160444 1/1964 Fed. Rep. of Germany .
2645085 4/1977 Fed. Rep. of Germany .
50-23090 8/1975 Japan .
51-31095 8/1976 Japan .

OTHER PUBLICATIONS

Wassaman et al., Chem. Abs. 91, 175088 (1979).
Hirata et al. Chem. Abs. 91, 39300 (1979).
Chemical Abstracts, "1972 Index Guide", p. 1484.

*Primary Examiner*—Mark L. Berch
*Attorney, Agent, or Firm*—Wolder, Gross & Yavner

[57] ABSTRACT

A 2-azetidinone of formula (I):

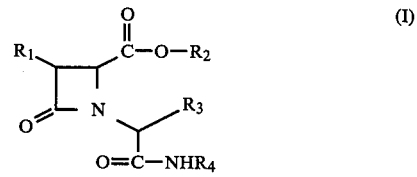

wherein $R_1$ represents an aralkoxy, acyloxy, sulphonyloxy or amino group any of which may be substituted, or hydrogen, hydroxy, alkoxy or azido;

$R_2$ represents an alkyl or aralkyl group either of which may be substituted, or hydrogen;

$R_3$ represents an alkyl, aryl, aralkyl, alkenyl, aralkenyl, alkynyl, aralkynyl, acyl or heterocyclic group any of groups may be substituted;

and $R_4$ represents an alkyl, alkenyl, aryl or aralkyl group any of which may be substituted;

or formula (I'):

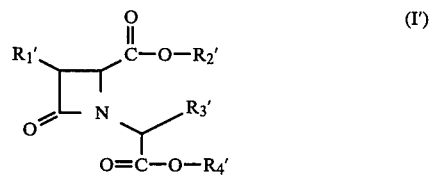

wherein $R_1'$ is the same as $R_1$ above;

$R_2'$ represents an alkyl, aralkyl or trialkylsilyl group any of which may be substituted, or hydrogen;

$R_3'$ is the same as $R_3$ above;

and $R_4'$ represents an alkyl, aralkyl or trialkylsilyl group any of which may be substituted, or hydrogen; provided that when $R_1'$ represents azido or optionally substituted amino, $R_2'$ represents hydrogen or $CH_2CCl_3$ and $R_4'$ represents

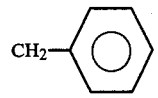

$R_3'$ represents other than

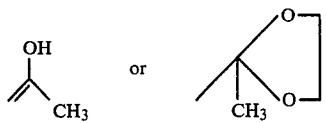

or a pharmaceutically acceptable salt thereof is disclosed. The derivatives exhibit β-lactamase inhibiting activity and are thus of interest as anti-bacterial agents, used alone or together with known antibiotic subtances.

22 Claims, 2 Drawing Figures

2-AZETIDINONE 4-CARBOXY DERIVATIVES AND A PROCESS FOR PRODUCING THE SAME

This is a continuation of application Ser. No. 947,223, filed Sept. 29, 1978, abandoned.

SUMMARY OF THE INVENTION

This invention relates to 2-azetidinone derivatives.

In general terms, the present invention provides a 2-azetidinone derivative corresponding to the following general formula (I):

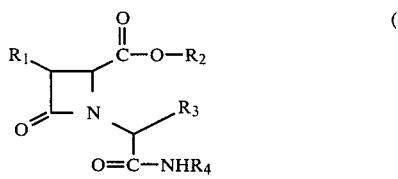

wherein $R_1$ represents an aralkoxy (e.g. benzyloxy), acyloxy (e.g. carbobenzoxy or acetyloxy), sulphonyloxy (e.g. p-toluene-sulphonyloxy or methanesulphonyloxy) or amino (e.g. dialkylamino, phthalylimino, alkylideneamino, carbobenzoxyamino or benzylamino) group any of which may be substituted one or more times (e.g. by halogen, lower alkyl, lower alkoxy or nitro) or hydrogen, hydroxy, alkoxy (e.g. tetrahydropyranyloxy or t-butoxy) or azido;

$R_2$ represents an alkyl (e.g. methyl, ethyl, i-propyl or n-, i- or t-butyl) or aralkyl (e.g. benzyl, diphenylmethyl, trityl or phthalidye) group either of which groups may be substituted one or more times (e.g. by halogen, lower alkyl, lower alkoxy or nitro) or hydrogen;

$R_3$ represents an alkyl (e.g. methyl, ethyl, n-, or i-butyl or pentyl) aryl (e.g. phenyl or naphthyl), aralkyl (e.g. benzyl), alkenyl (e.g. ethenyl, 1- or 2-propyl or 3-butenyl), aralkenyl (e.g. styryl or cinnamyl), alkynyl (e.g. ethynyl, 1- or 2-propynyl or 1- or 2-butynyl), aralkynyl (e.g. 2-phenyl-1-ethynyl), acyl (e.g. acetyl, propionyl or butyryl), or heterocyclic group (e.g. 2- or 3-furyl, 2- or 3-thienyl, 2- or 3-pyrrolyl, 2- or 4-imidazolyl, 3-pyrazolyl, 4-isoxazolyl, 2-, 3-, 4-, 5-, 6- or 7-indolyl or 2- or 3-benzo (b) furanyl), any of which groups may be substituted one or more times (e.g. by halogen, lower alkyl, lower alkoxy, lower acyloxy, hydroxy, optionally substituted amino, optionally substituted thio or nitro);

$R_4$ represents an alkyl (e.g. methyl, ethyl, i-propyl, pentyl or n-, i- or t-butyl), alkenyl (e.g. ethenyl, 1- or 2-propenyl or 3-butenyl), aryl (e.g. phenyl or naphthyl) or aralkyl (e.g. benzyl, diphenylmethyl, trityl or phthalidyl) group any of which groups may be substituted one or more times (e.g. by halogen, lower alkyl, lower alkoxy, lower acyloxy, hydroxy, optionally substituted amino, optionally substituted thio or nitro); or corresponding to the following general formula (I'):

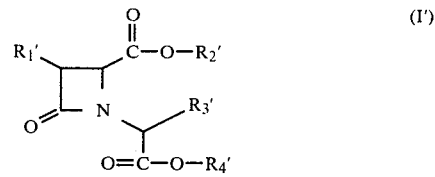

wherein $R_1'$ represents an aralkoxy (e.g. benzyloxy), acyloxy (e.g. carbobenzoxy or acetyloxy), sulphonyloxy (e.g. p-toluene-sulphonyloxy or methanesulphonyloxy) or amino (e.g. dialkylamino, phthalylimino, alkylideneamino, carbobenzoxyamino or benzylamino) group any of which may be substituted one or more times (e.g. by halogen, lower alkyl, lower alkoxy or nitro) or hydrogen, hydroxy, alkoxy (e.g. tetrahydropyranyloxy or t-butoxy) or azido;

$R_2'$ represents an alkyl (e.g. methyl, ethyl, i-propyl or n-, i- or t-butyl), aralkyl (e.g. benzyl, diphenylmethyl, trityl or phthalidyl) or trialkylsilyl group any of which groups may be substituted one or more times (e.g. by halogen, lower alkyl, lower alkoxy or nitro) or hydrogen;

$R_3'$ represents an alkyl (e.g. methyl, ethyl, n- or i-butyl or pentyl), aryl (e.g. phenyl or naphthyl), aralkyl (e.g. benzyl), alkenyl (e.g. ethenyl, 1- or 2-propenyl or 3-butenyl), aralkenyl (e.g. styryl or cinnamyl), alkynyl (e.g. ethynyl, 1- or 2-propynyl or 1- or 2-butynyl), aralkynyl (e.g. 2-phenyl-1-ethynyl), acyl (e.g. acetyl, propionyl or butyryl) or heterocyclic group (e.g. 2- or 3-furyl, 2- or 3-thienyl, 2- or 3-pyrrolyl, 2- or 4-imidazolyl, 3-pyrazolyl, 4-isoxazolyl, 2-, 3-, 4-, 5-, 6- or 7-indolyl or 2- or 3-benzo (b) furanyl) any of which group may be substituted one or more times (e.g. by halogen, lower alkyl, lower alkoxy, lower acyloxy, hydroxy, optionally substituted amino, optionally substituted thio or nitro);

and $R_4'$ represents an alkyl, (e.g. methyl, ethyl i-propyl or n-, i- or t-butyl), aralkyl (e.g. benzyl, diphenylmethyl, trityl or phthalidyl) or trialkylsilyl group any of which groups may be substituted one or more times (e.g. by halogen, lower alkyl, lower alkoxy or nitro) or hydrogen;

or a pharmaceutically acceptable salt thereof.

Also, in general terms, the present invention provides an optically active form of such a derivative corresponding to the following general formula (Ia):

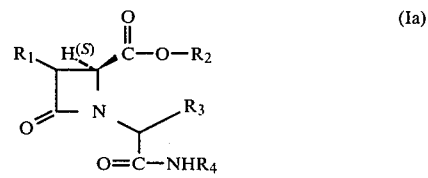

wherein $R_1$, $R_2$, $R_3$ and $R_4$ are as defined above; or corresponding to the following general formula (I'a):

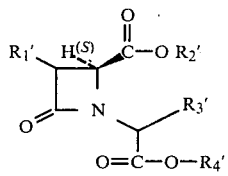

(I'a)

wherein
$R_1'$, $R_2'$, $R_3'$ and $R_4'$ are as defined above; or a pharmaceutically acceptable salt thereof.

In a first embodiment, the present invention provides a 2-azetidinone derivative corresponding to the following general formula (II):

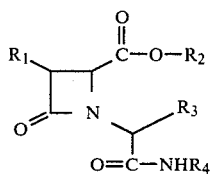

(II)

wherein
$R_1$ represents an aralkoxy, acyloxy, sulphonyloxy or amino group any of which groups may be substituted one or more times or hydrogen, hydroxy, alkoxy or azido;

$R_2$ represents an alkyl or aralkyl group either of which groups may be substituted one or more times;

$R_3$ represents an alkyl, aryl, aralkyl, alkenyl, aralkenyl, alkynyl, aralkynyl or acyl group any of which groups may be substituted one or more times;
and $R_4$ represents an alkyl, alkenyl, aryl, or aralkyl group any of which groups may be substituted one or more times.

This embodiment of the present invention also provides an optically active form of such a derivative corresponding to the following general formula (IIa):

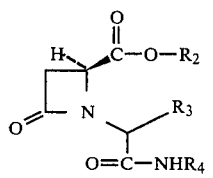

(IIa)

wherein
$R_2$, $R_3$ and $R_4$ are as defined above.

In a second embodiment, the present invention provides a 2-azetidinone derivative corresponding to the following general formula (III):

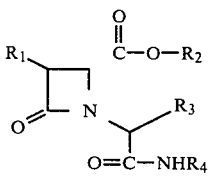

(III)

wherein
$R_1$ represents an aralkoxy, acyloxy, sulphenyloxy or amino group any of which groups may be substituted one or more times or hydrogen, hydroxy, alkoxy or azido;

$R_2$ represents an alkyl or aralkyl group either of which groups may be substituted one or more times;

$R_3$ represents an alkyl, aryl, aralkyl, alkenyl, aralkenyl, alkynyl, aralkynyl, acyl or heterocyclic group any of which groups may be substituted one or more times;
and $R_4$ represents an alkyl, alkenyl, aryl or aralkyl group any of which groups may be substituted one or more times.

This embodiment of the present invention also provides an optically active form of such a derivative corresponding to the following general formula (IIIa):

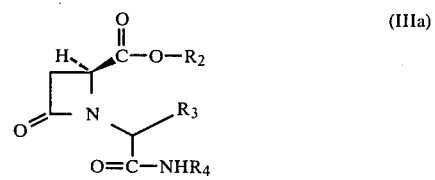

(IIIa)

wherein
$R_2$, $R_3$ and $R_4$ are as defined above.

In a third embodiment, the present invention provides a 2-azetidinone derivative corresponding to the following general formula (IV):

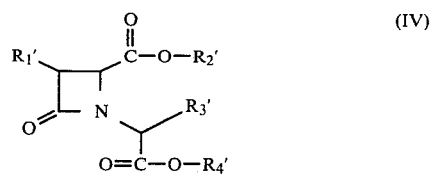

(IV)

wherein
$R_1'$ represents an aralkoxy, acyloxy or sulphonyloxy group any of which groups may be substituted one or more times or hydrogen, alkoxy, azido or disubstituted amino;

$R_2'$ represents an alkyl, aralkyl or trialkylsilyl group any of which groups may be substituted one or more times or hydrogen;

$R_3'$ represents an alkyl, aryl, aralkyl, alkenyl, aralkenyl, alkynyl, aralkynyl, acyl or heterocyclic group any of which groups may be substituted one or more times;
and $R_4'$ represents an alkyl, aralkyl or trialkylsilyl group any of which groups may be substituted one or more times or hydrogen;
or a pharmaceutically acceptable salt thereof.

This embodiment of the present invention also provides an optionally active form of such a derivative corresponding to the following general formula (IVa):

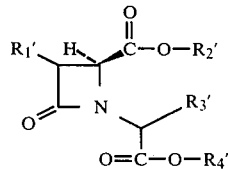

wherein
$R_1'$, $R_2'$, $R_3'$ and $R_4'$ are as defined above; or a pharmaceutically acceptable salt thereof.

Regarding the compounds corresponding to above general formulae (I), (Ia), (II), (IIa), (III) and (IIIa), when $R_3$ represents an acyl group corresponding to the following general formula:

wherein
$R_5$ represents $C_2$–$C_5$ alkyl; at least part of these compounds is present in the following end form conjugated with a secondary amide:

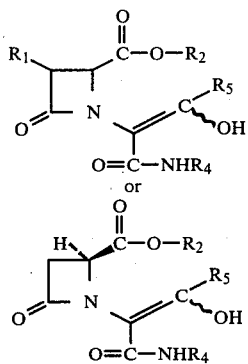

Preferred examples of pharmaceutically acceptable salts of the above compounds include metallic salts obtained using, as at least one member of $R_2$, $R_2'$, $R_4$ or $R_4'$, an alkali metal (e.g. sodium or potassium) or an alkaline earth metal (e.g. calcium or magnesium) and salts obtained using an organic base (e.g. triethylamine, dicyclohexylamine, morpholine, piperidine or pyridine).

The derivatives corresponding to the above general formulae exhibit β-lactamase inhibiting activity and are thus of interest as anti-bacterial agents. For example, they may be used alone or together with known antibiotic substances, such as cephalosporins and penicillins, for treating various infectious diseases.

They may also be used as intermediates in the preparation of other similar derivatives.

For example, they may be used in the preparation of bicyclic β-lactam antibiotic substances such as O-2-isocephem compounds corresponding to the following general formula (reported by T. W. Doyle et al, Can. J. Chem., 55, 484, (1977)) and analogues thereof:

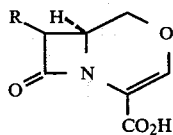

The present invention is based upon the discovery that various antibiotic substances of β-lactam type and skeletal analogues thereof possess commonly a certain absolute configuration at the 4th position of the 2-azetidinone which appears to be essential for exhibiting activity against bacteria and β-lactamase.

β-lactamase inhibiting activities of some compounds according to the present invention were determined by using β-lactamase produced by Enterobacter sp. KY 3073 and chromogenic cephalosporin as substrate in a similar manner to that described in Antimicrobial Agent and Chemotherapy, Vol. 1, 283, (1972) to give the following results:

| Compound of | | Concentration (μg/ml) | Inhibition activity % |
|---|---|---|---|
| Example | 6 | 50 | 50 |
| | 7 | 100 | 50 |
| | 9 | 50 | 18 |
| | 11 | 50 | 15 |
| | 12 | 50 | 22 |
| | 14 | 50 | 20 |
| | 15 | 50 | 34 |

In one embodiment, the present invention further provides a process for the preparation of a derivative corresponding to above general formulae (I), (Ia), (II), (IIa), (III) and (IIIa) which comprises condensing, in a solvent, an aspartic acid derivative corresponding to the following general formula:

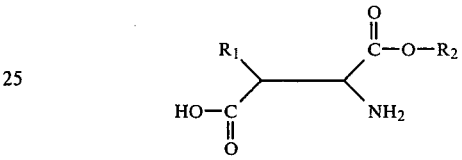

an aldehyde corresponding to the following general formula:

$R_3CHO$ and an isonitrile corresponding to the following general formula:
$R_4N\!\!\equiv\!\!C$ wherein
$R_1$, $R_2$, $R_3$ and $R_4$ are as defined above.

In another embodiment, the present invention further provides a process for the preparation of a derivative corresponding to above general formulae (I'), (I'a), (IV) and (IVa) which comprises reacting a 2-azetidinone derivative corresponding to the following general formula:

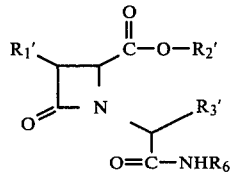

wherein
$R_1'$, $R_2'$ and $R_3'$ are as defined above;
and
$R_6$ represents an alkyl, alkenyl, aryl or aralkyl group any of which groups may be substituted one or more times;
with a halogenating agent to give an imidoylhalide, reacting the imidoylhalide with an appropriate alcohol or alkoxide to give an iminoether derivative and hydrolysing the iminoether derivative.

The present invention also relates to the thus prepared derivatives and to pharmaceutical compositions comprising such derivatives and pharmaceutically acceptable carriers or diluents and optionally penicillins or cephalosporins. The present invention further relates to the use of such derivatives or such compositions for inhibiting β-lactamase activity.

In more general terms now, the derivatives corresponding to the following general formula:

$$\underset{O}{\overset{R_7}{\diagdown}}\underset{N}{\overset{CO_2R_8}{\diagup}}\underset{CO_2R_{10}}{\overset{R_9}{\diagup}} \quad (A)$$

wherein
$R_7$ represents hydrogen, hydroxy, alkoxy, optionally substituted aralkyloxy, optionally substituted acyloxy, optionally substituted sulphonyloxy, optionally substituted amino or azido;
$R_8$ and $R_{10}$, which may be the same or different, each represents hydrogen, optionally substituted alkyl or optionally substituted aralkyl;
and
$R_9$ represents an alkyl, aryl, aralkyl, alkenyl, aralkenyl, alkynyl, aralkynyl, heterocyclic or acyl group, each of which may optionally be substituted;
or optionally active derivatives corresponding to the following general formula:

$$\underset{O}{\overset{R_7\,\,H^{(S)}}{\diagdown}}\underset{N}{\overset{CO_2R_8}{\diagup}}\underset{CO_2R_{10}}{\overset{R_9}{\diagup}} \quad (B)$$

wherein
$R_7$, $R_8$, $R_9$ and $R_{10}$ are as defined above; may be prepared by treating a 2-azetidinone derivative corresponding to one of the following general formulae:

$$\underset{O}{\overset{R_7'}{\diagdown}}\underset{N}{\overset{CO_2R_8'}{\diagup}}\underset{CONHR_{11}}{\overset{R_9}{\diagup}} \quad \underset{O}{\overset{R_7'\,\,H^{(S)}}{\diagdown}}\underset{N}{\overset{CO_2R_8'}{\diagup}}\underset{CONHR_{11}}{\overset{R_9}{\diagup}}$$
(C) \qquad\qquad (D)

wherein
$R_7'$ represents hydrogen, alkoxy, optionally substituted aralkyloxy, optionally substituted acyloxy, optionally substituted sulphonyloxy, di-substituted amino or azido;
$R_8'$ represents an optionally substituted alkyl or optionally substituted aralkyl group;
$R_9$ is as defined above;
and
$R_{11}$ represents an alkyl, alkenyl, aryl or aralkyl group, each of which may optionally be substituted;
[however, when $R_9$ represents an acyl group in enol form, the enol of $R_9$ may be protected by an acyl group (e.g. enol acetate) or alkyl group (e.g. enol methyl ester)]; with a halogenating agent to form a corresponding imidoylhalide derivative, treating the imidoylhalide derivative with an alcohol or alkoxide to form an iminoether derivative, subjecting the same to the hydrolysis and, if desired, removing the protective group from the carboxyl, amino or hydroxy group in conventional manner.

The derivatives corresponding to the above general formulae (C) and (D) may be prepared by carrying out, in a suitable solvent a condensation reaction of an aspartic acid derivative corresponding to the following general formula:

$$\underset{HO_2C}{\overset{R_{12}}{\diagdown}}\underset{NH_2}{\overset{CO_2R_8'}{\diagup}}$$

wherein
$R_{12}$ represents hydrogen, hydroxy, alkoxy, optionally substituted aralkyloxy, optionally substituted sulphonyloxy, substituted amino or azido; and
$R_8'$ is as defined above; with an aldehyde corresponding to the following general formula:

$R_9CHO$ wherein $R_9$ is as defined above; and an isonitrile corresponding to the following general formula:

$R_{11}N\!\!=\!\!C$ wherein $R_{11}$ is as defined above; and, if desired, removing the protective group from the carboxylic group or amino group.

By the process according to the present invention, a secondary amide derivative is converted into an iminoether-type compound which is then converted into an ester-type compound. The application of such a method to the preparation of 2-azetidinone derivatives is now proposed for the first time although this method is known in connection with other compounds. For example, analogous methods have been applied to the amidolysis of acylated 7-aminocephalosporanic acid derivatives, but such methods were not directed to the production of esters, but to the production of amino compounds. In other words, such methods were used to obtain an amino group attached to the 3rd position of a 2-azetidinone moiety, as reported, for example, in Helv. Chim. Acta., 51, p. 1108 (1968); J. Org. Chem. 36, p. 1259 (1971); J. Antibiotics, 25, p. 248 (1972); and published Japanese Patent Application Nos. 23090/77 and 31095/77.

Reference may also be made in this connection to German Auslegeschrift No. 1,160,444.

Alternatively, the derivatives corresponding to above-defined general formulae (A) or (B) may be prepared by converting an ester group of a derivative corresponding to one of the following general formulae:

$$\underset{O}{\overset{R_7'}{\diagdown}}\underset{N}{\overset{CO_2R_8'}{\diagup}}\underset{CO_2R_{13}}{\overset{R_9}{\diagup}} \quad (E)$$

$$\underset{O}{\overset{R_7'\,\,H^{(S)}}{\diagdown}}\underset{N}{\overset{CO_2R_8'}{\diagup}}\underset{CO_2R_{13}}{\overset{R_9}{\diagup}} \quad (F)$$

wherein $R_7'$, $R_8'$ and $R_9$ are as defined above; and
$R_{13}$ represents alkyl or aralkyl;
selectively into the corresponding carboxyl group. In this case, it is possible to select, depending upon the types of the groups $R_8'$ and $R_{13}'$, various techniques of the known types, for example, the reaction conditions (e.g. the intensity of the reagents (acid and base), reaction temperature and time and agents used for hydrolysis, reduction, hydrogenation or dealkylation).

In a preferred embodiment of the present process, the hydrogenation of a compound corresponding to general formulae (E) or (F) (wherein $R_8'$ represents benzyl and $R_{13}$ represents methyl) may be effected by using a palladium-carbon catalyst so that the hydrogenolysis of the group —$COOR_8'$ is selectively effected to form a compound (A) or (B) (wherein $R_8$ represents hydrogen $R_{10}$ represents methyl) as monocarboxylic acid. On the other hand, when a compound (E) or (F) (wherein $R_8'$ represents t-butyl and $R_{13}$ represents methyl) is used for the reaction, the group —$COOR_{13}$ is selectively hydrolized in the presence of a potassium carbonate catalyst to form a compound (A) or (B) (wherein $R_8$ represents t-butyl and $R_{10}$ represents hydrogen) as monocarboxylic acid.

When a compound (A) or (B) wherein either of $R_8$ or $R_{10}$ represents hydrogen is prepared, it is advantageous to use as a starting material a compound wherein one of $R_8$ or $R_{10}$ may more readily be converted into a carboxylic acid than the other.

It is particularly advantageous to select $R_8$ so that the group may be converted to a carboxylic acid group without undesirable side-effects upon other parts of the molecule, because those compounds wherein only the $R_8$ group has been converted to a carboxylic acid group are particularly useful as intermediates.

The derivatives (A) may be prepared by treating a compound (C) with a halogenating agent to form a corresponding iminohalide, treating the iminohalide with an alcohol or alkoxide of an alkali metal to form an iminoether and subjecting the same to the hydrolysis. In this process, the reaction proceeds as follows.

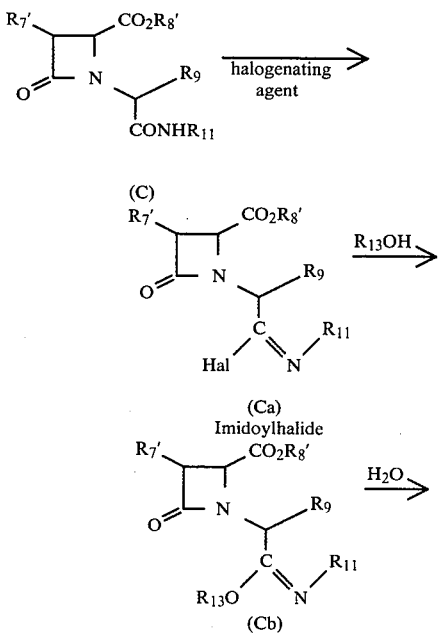

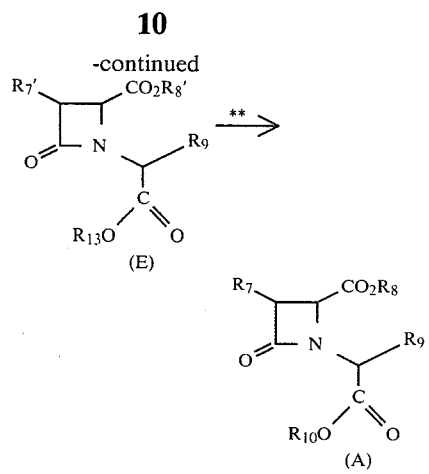

In this process, it is possible, if desired, to remove the protective group from a carboxyl, amino or hydroxy group in conventional manner, as shown by the line marked**.

The above-mentioned reaction may proceed continuously in a same solvent and thus the intermediates are usually not isolated. Examples of the inert solvents which may be used include: chloroform, dichloromethane, dichloroethane, benzene, diethyl ether, tetrahydrofuran and dioxane. The starting materials are usually used in an amount of from 1 millimole to 2 mole preferably from 10 millimole to 0.5 mole, per liter of solvent. Examples of the halogenating agents which may be used include: phosphorus pentachloride, phosphorus oxychloride, thionyl chloride, phosgene, oxalylchloride and a complex of dichlorophenylphosphine and chlorine; it is preferred to use phosphorus pentachloride.

The amount of halogenating agent used is generally from 1 to 10 mole, preferably from 1 to 2 mole, per mole of compound. Depending upon the type of starting materials used and other conditions, the reaction temperature and time may vary from $-78°$ to $+150°$ C., preferably from $-10°$ to $+50°$ C., for a period of from 10 minutes to 24 hours. In the reaction, it is possible to use as a catalyst a base, such as a tertiary amine, e.g. triethylamine, pyridine, quinoline or dimethylaniline. Generally, the amount of base used may vary, depending upon the amount of the halogenating agent used and other conditions, from 1 to 50 mole, preferably from 1 to 20 mole, per mole of the starting materials.

Examples of the alcohols and alkoxides which may be used include: lower alkyl alcohols, e.g. methanol or isobutanol and lower haloalkyl alcohols and alkoxides obtained using such alcohols and alkali metals. Usually, an excess of alcohol is used, e.g. from 20 to 1000 mole per mole of the starting materials, while the amount of alkoxide used may vary, depending upon the amount of halogenating agent used in the foregoing steps, preferably from 2 to 50 mole.

The reaction temperature and time may vary, depending, for example, upon the type of halogenating agent, base, alcohol or alkoxide used, from $-78°$ to $+150°$ C., preferably from $-40°$ to $+50°$ C., for a period of from 10 minutes to 48 hours.

The ester (E) is obtained by treating the produced iminoether with an acidic aqueous solution, water or an alkaline aqueous solution, depending, for example, upon $R_{11}$ and the reaction conditions in the foregoing steps. An especially good result may be obtained by using an aqueous solution of HCl (from 0.1 to 1.0 N) and in this case the reaction is preferably effected at from −10° to +50° C. for from 5 minutes to 12 hours.

DRAWINGS

Figure 2:
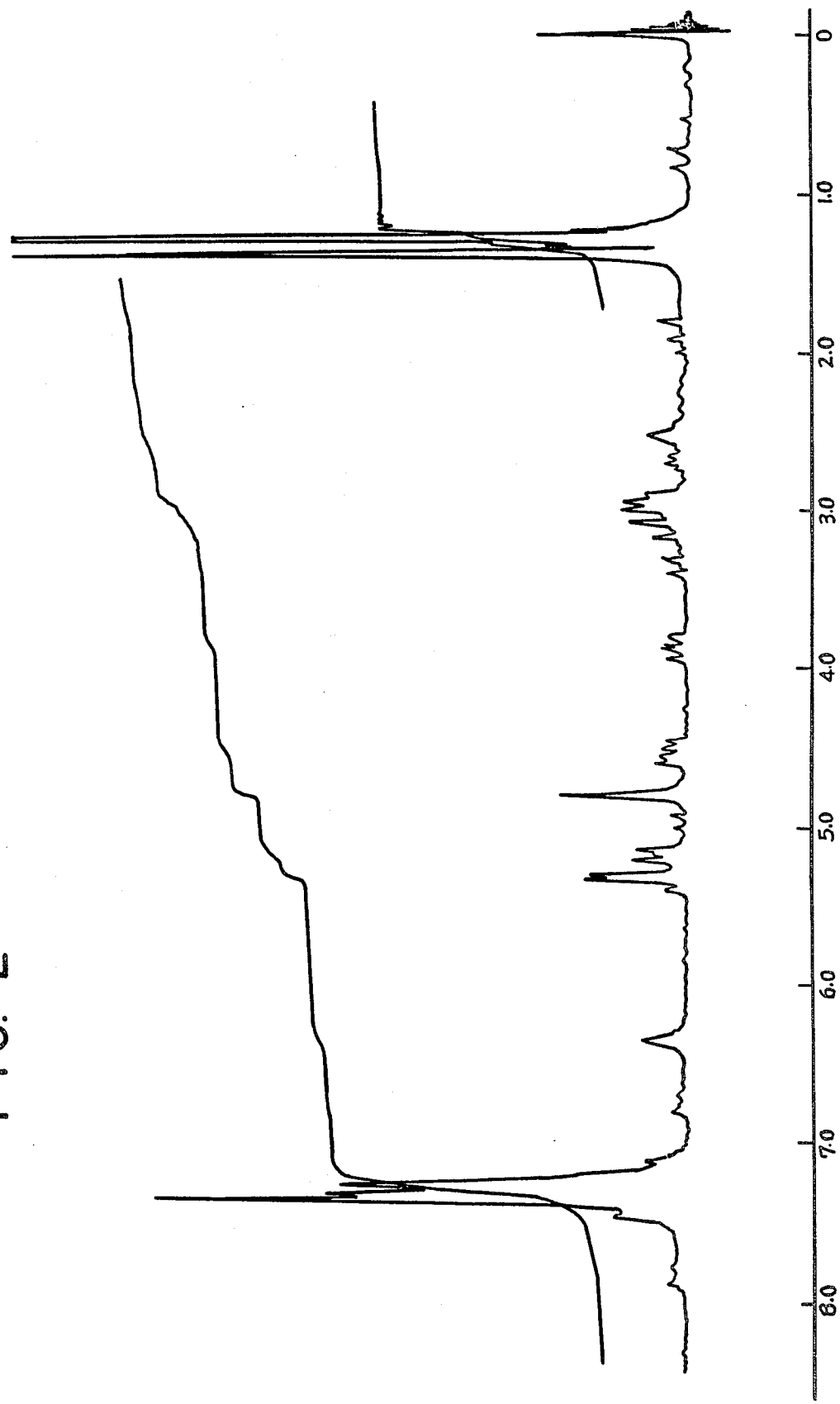

FIGS. 1 and 2 show the N.M.R. spectra of 2-azetidinone derivatives prepared in Examples 3 and 4, respectively.

PREFERRED EMBODIMENTS

The following non-limitative examples illustrate the invention.

(Unless otherwise indicated, all products are white to light yellow in colour.)

EXAMPLE 1

Preparation of (4S)-t-butyl-α-(4-benzyloxycarbonyl-2-oxo-azetidine-1-yl)-α-(acetyl) acetamide, i.e.

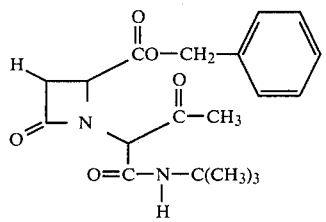

L-aspartic acid-α-benzyl ester (634 mg, 2.84 millimole) suspended in methanol (10 ml) was added to 40% aqueous pyruvaldehyde (0.28 ml 1.5 millimole) and t-butylisonitrile (250 mg, 3.0 millimole) and was stirred under nitrogen at room temperature for 48 hours. After completion of the reaction, the solution was filtered to remove insoluble materials and the filtrate was distilled under reduced pressure to remove the solvent. The thus-obtained oily substance was then transferred to a column (diameter about 2 cm) packed with 30 g of silica gel (Q23 obtainable from Wako Junyaku K.K. Japan) and was purified by column-chromatography using a solvent system of hexane/ethyl acetate (1:1 by volume). The eluate was divided into 8 ml fractions. Fractions 9 to 30 were collected and combined. The solvent was removed from the combined fractions by distillation under reduced pressure to yield an oily substance (515 mg) having the following physical characteristics.

Elemental analysis as $C_{19}H_{24}N_2O_5$ (molecular weight 360.40):

|  | C | H | N |
|---|---|---|---|
| Calculated: (%) | 63.32 | 6.71 | 7.77 |
| Observed: (%) | 63.41 | 7.02 | 7.73 |

Specific rotation: $[\alpha]_D^{23} = -66.9$ (CHCl$_3$, C = 1.63)
Infra-red absorption spectrum: $\gamma_{max}^{CHCl_3}$(cm$^{-1}$)
1780, 1745, 1680, 1625
N.M.R. spectrum: δCDCl$_3$
1.33; 1.37 (2S 9H) 1.87 (brs 1.88H) 2.03 (brs 0.3H) 2.30 (brs 0.82H) 2.63–3.53 (m 2H) 4.1–4.73 (m 1H) 4.92 (brs 0.1H) 5.23 (brs 2H) 7.33 (brs 1H) 15.13 (brs 0.9H)
Thin layer chromatography:
Using a silica gel plate (Merck) and benzene/acetone (1:1 by volume), a single spot was observed (Rf = 0.70).

From these data, the oily substance obtained was identified as (4S)-t-butyl-α-(4-benzyloxycarbonyl-2-oxoazetidine-1-yl)-α-(acetyl) acetamide [yield: 50.3%]. When subjected to the FeCl$_3$ colour reaction on the thin layer chromatography plate, this substance becomes brown. Also the N.M.R. spectrum reveals a signal of a proton at δ15.13 which is exchangeable with deuterated methanol.

These facts indicate the presence of this substance mainly in enol form.

EXAMPLE 2

Preparation of (4S)-t-butyl-α-(4-methoxycarbonyl-2-oxoazetidine-1-yl)-α-(styryl) acetamide, i.e.

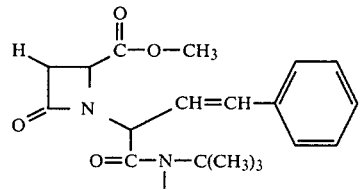

L-aspartic acid-α-methyl ester (405 mg 2.76 millimole) suspended in methanol (8 ml) was added to cinnamaldehyde (0.38 ml, 3.0 millimole) and t-butylisonitrile (250 mg 3.0 millimole) and was stirred under nitrogen at room temperature for 48 hours. After completion of the reaction, the solvent was evaporated off under reduced pressure and the residue was washed using a solvent of ethyl acetate and hexane (20 ml; 2:1, by volume). The resulting solution was concentrated under reduced pressure and was then transferred to a column (diameter about 2 cm) packed with 60 g of silica gel (Q23). The purification was effected by column chromatography using a solvent system of ethyl acetate hexane (1:1 by volume) and the eluate was divided into 3 ml fractions. Fractions 28 to 120 were collected and combined. The combined fractions were distilled under reduced pressure to remove the solvent giving a white powder (90 mg) having the following physical characteristics.

Elemental analysis as $C_{19}H_{24}N_2O_4$ (molecular weight 344.40):

|  | C | H | N |
|---|---|---|---|
| Calculated (%): | 66.26 | 7.02 | 8.13 |
| Observed (%): | 66.16 | 7.06 | 7.95 |

Specific rotation: $[\alpha]_D^{23} = -60.0$ (CHCl$_3$, C = 0.02)
Infra-red absorption spectrum: $\gamma_{max}^{CHCl_3}$(cm$^{-1}$)
1760 (br), 1680
N.M.R. spectrum: δCD$_3$OD
Note:- ( ) indicates the coupling constant (Hz) 1.33 (brs 9H) 2.94–3.39 (m 2H) 3.63 (S 1.14H) 3.79 (S 1.86H) 4.43 (m 1H) 4.88 [d 1H(6)] 6.24 [dd 1H (6, 16)] 6.74 [dd 1H (2, 16)] 7.33 (brs 5H)
Thin layer chromatography:
Using a silica gel plate (Merck) and benzene/ethyl acetate (1:1 by volume) single spot was observed (Rf = 0.50).

From these data, the thus-obtained white powder was identified as (4S)-t-butyl-α-(4-methoxycarbonyl-2-oxoazetidine-1-yl)-α-(styryl) acetamide [yield: 9.5%].

EXAMPLE 3

Preparation of (4S)-t-butyl-α-(4-methoxycarbonyl-2-oxoazetidine-1-yl)-α-(isopropyl) acetamide i.e.

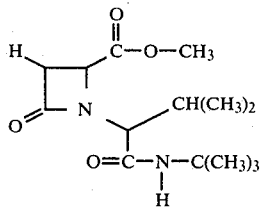

L-aspartic acid-α-methylester (405 mg 2.76 millimole) suspended in methanol (8 ml) was added to isobutylaldehyde (216 mg 3.0 millimole) and t-butylisonitrile (250 mg 3.0 millimole) and was stirred under nitrogen at room temperature for 16 hours. After this, the solvent was removed by distillation under reduced pressure to give an oily substance which was transferred to a column (diameter about 2 cm) packed with 60 g of silica gel (Q23). The purification was effected by column chromatography: 200 ml of a solvent system of hexane and ethyl acetate (1:1 by volume) is passed through the column and then elution is effected using a solvent of hexane/ethyl acetate (1:2 by volume). The effluent is divided into 8 ml fractions and fractions 35 to 65 are collected and combined. The solvent is evaporated off under reduced pressure to give a colourless oily substance (520 mg) having the following physical characteristics.

Elemental analysis as $C_{14}H_{24}N_2O_4$ (molecular weight 284.35):

|  | C | H | N |
|---|---|---|---|
| Calculated (%): | 59.14 | 8.51 | 9.85 |
| Observed (%): | 59.10 | 8.58 | 9.67 |

Specific rotation: $[\alpha]_D^{23} = -69.1$ (CHCl$_3$, C = 1.37)
Infra-red absorption spectrum: $\gamma_{max}^{CHCl_3}$(cm$^{-1}$)
    1755 (br), 1680
N.M.R. spectrum: in CDCl$_3$
    as shown in Figure 1
Thin layer chromatography:
    Using a silica gel plate (Merck) and benzene/ethyl acetate (1:1, by volume), a single spot was observed (Rf = 0.44).

From these data, the oily substance obtained was identified as (4S)-t-butyl-α-(4-methoxycarbonyl-2-oxoazetidine-1-yl)-α-(isopropyl) acetamide [yield 66.2%].

EXAMPLE 4

Preparation of (4S)-t-butyl-α-(4-benzyloxycarbonyl-2-oxo-azetidine-1-yl)-α-(phenyl) acetamide i.e.

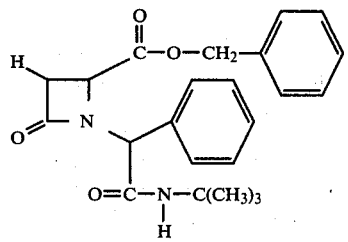

L-aspartic acid-α-benzyl ester (634 mg, 3 millimole) was suspended in methanol (10 ml). The suspension was then added to benzaldehyde (318 mg, 3 millimole) and t-butyl-isonitrile (250 mg, 3 millimole). The mixture was stirred under nitrogen at room temperature for 17 hours. After completion of the reaction, the solvent was evaporated off and the residue was washed using a solvent mixture (20 ml) of ethyl acetate/petroleum ether (20 ml, 1:10, by volume). The washing solution was concentrated under reduced pressure and was then purified by column chromatography using Q23 silica gel (60 g). A solvent system of benzene/ethyl acetate (3:1, by volume) was used and the eluate was divided into 3 ml fractions. Fractions 28 to 60 were collected and combined and the solvent was removed by distillation under reduced pressure to give an oily substance (380 mg) having the following physical characteristics.

Elemental analysis as $C_{23}H_{26}N_2O_4$ (molecular weight 394.45):

|  | C | H | N |
|---|---|---|---|
| Calculated (%): | 70.63 | 6.64 | 7.10 |
| Observed (%): | 70.51 | 6.56 | 7.11 |

Specific rotation: $[\alpha]_D^{23} = -65.4$ (CHCl$_3$, C = 0.77)
Infra-red absorption spectrum: $\gamma_{max}^{CHCl_3}$(cm$^{-1}$)
    1770, 1740-60 (sh), 1680
N.M.R. spectrum: (in CDCl$_3$) as shown in FIG. 2
Thin layer chromatography:
    Using a silica gel plate (Merck) and benzene/ethyl acetate (1:1, by volume), a single spot was observed (Rf = 0.60).

From these data, the oily substance obtained was identified as (4S)-t-butyl-α-(4-benzyloxycarbonyl-2-oxo-azetidine-1-yl)-α-(phenyl) acetamide [yield 32.1%].

EXAMPLE 5

Preparation of (4S)-ethyl-α-(4-methoxycarbonyl-2-oxoazetidine-1-yl)-α-(acetyl) acetamide i.e.

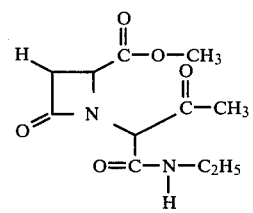

L-aspartic acid-α-methyl ester (802 mg, 5.45 millimole) suspended in methanol (20 ml) was added to 40% aqueous pyruvaldehyde (0.61 ml, 3.27 millimole) and ethylisonitrile (300 mg, 5.45 millimole) and was stirred under nitrogen at room temperature for 18 hours. After completion of the reaction, the solvent was evaporated off. The residue was added to water (20 ml) and was extracted using three 20 ml portions of ethyl acetate. The extract was washed twice using 10 ml portions of a saturated solution of sodium chloride and was dried over Glauber's salt. The solvent was distilled off under reduced pressure to give an oily substance which is transferred to a column (diameter about 5 cm) packed with 150 g of silica gel (Q23). The purification was effected by column chromatography. Hexane/ethyl acetate (700 ml, 1:1 by volume) was passed through the column and elution was effected using a solvent mixture of hexane/ethyl acetate (1:3 by volume). The eluate was divided into 8 ml fractions and fractions 96 to 145 were collected and combined and the solvent was evaporated off under reduced pressure to yield an oily substance (240 mg) having the following physical characteristics.

Elemental analysis as $C_{11}H_{16}N_2O_5$
(molecular weight 256.25):

|  | C | H | N |
|---|---|---|---|
| Calculated (%): | 51.56 | 6.29 | 10.93 |
| Observed (%): | 51.41 | 6.20 | 10.65 |

Specific rotation: $[\alpha]_D^{23} = -86.5$ (CHCl$_3$, C = 2.0)
Infra-red absorption spectrum: $\gamma_{max}^{CHCl_3}$ (cm$^{-1}$)
1780, 1745, 1680, 1630
N.M.R. spectrum: δ CDCl$_3$
  Note: ( ) indicates the coupling
  constant (Hz). 1.17 [t 3H (S)] 1.97
  (S 1.94H) 2.03 (S 0.59H) 2.30 (m 0.48H),
  2.66–3.59 (m 4H) 3.83 (S 3H) 4.30 (m 1H)
  5.06 (brs 0.2H) 7.10 (brs 1H) 14.97 (brs 0.8H)
Thin layer chromatography:
  Using a silica gel plate (Merck) and
  benzene/ethyl acetate (1:1 by volume), a single
  spot was observed (Rf = 0.33).

From these data, this oily substance was identified as (4S)-ethyl-α-(4-methoxycarbonyl-2-oxoazetidine-1-yl)-α-(acetyl) acetamide. When subjected to the FeCl$_3$ colour reaction on the thin layer chromatography plate, this substance becomes brown. Also, the N.M.R. spectrum reveals a signal of a proton (δ14.97) which is exchangeable with deuterated methanol.

These facts indicate the presence of this substance mainly in enol form.

EXAMPLE 6

Preparation of (4S)-ethyl-α-(4-benzyloxycarbonyl-2-oxoazetidine-1-yl)-α-(acetyl) acetamide, i.e.

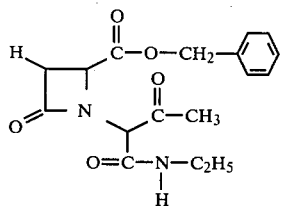

L-aspartic acid-α-benzyl ester (1.27 g, 5.7 millimole) suspended in methanol (20 ml) was added to 40% aqueous pyruvaldehyde (0.56 ml, 3.0 millimole) and ethylisonitrile (330 mg, 6.0 millimole). The mixture was stirred at room temperature for 48 hours, followed by stirring at 45° C. for 2 hours. After the removal of insoluble materials, the solvent was removed by distillation under reduced pressure. An oily substance was obtained, which was transferred to a column (diameter about 4 cm) packed with 120 g of silica gel (Q23) to effect purification by column chromatography. A solvent mixture of benzene and ethyl acetate (160 ml 5:1 by volume) was passed through the column and then elution was effected using a solvent mixture of benzene and ethyl acetate (2:1 by volume). The eluate was divided into 8 ml fractions. Fractions 45 to 90 were collected and combined and the solvent was evaporated off under reduced pressure to yield an oily substance (350 mg) having the following physical characteristics.

Elemental analysis as $C_{17}H_{20}N_2O_5$
(molecular weight 332.35):

|  | C | H | N |
|---|---|---|---|
| Calculated (%): | 61.44 | 6.07 | 8.43 |
| Observed (%): | 61.65 | 6.28 | 8.43 |

Specific rotation: $[\alpha]_D^{23} = -66.7$ (CHCl$_3$, C = 0.86)
Infra-red absorption spectrum: $\gamma_{max}^{CHCl_3}$ (cm$^{-1}$)
1780, 1740, 1690, 1625
N.M.R. spectrum: δ CDCl$_3$
  Note: ( ) indicates the coupling
  constant (Hz), 1.17 [t 3H (8)] 1.94
  (S 2.22H) 2.06 (S 0.36H) 2.26 (S 0.42H)
  3.03–3.59 (m 2H) 4.36 (m 1H) 5.23 (S 2H)
  7.13 (brs 1H) 7.36 (S 5H) 14.95 (brs 1H)
Thin layer chromatography:
  Using a silica gel plate (Merck) and
  benzene/ethyl acetate (1:1 by volume), a single
  spot (Rf = 0.53) was observed.

From these data, this oily substance was identified as (4S)-ethyl-α-(4-benzyloxycarbonyl-2-oxoazetidine-1-yl)-α-(acetyl) acetamide. This substance becomes brown on being subjected to the FeCl$_3$ colour reaction on the thin layer chromatography plate, while the N.M.R. spectrum reveals a signal of a proton (δ14.95) which is exchangeable with deuterated methanol.

These facts indicate the presence of this substance mainly in enol form.

EXAMPLE 7

Preparation of 3,4-erythro-ethyl-α-(4-t-butoxycarbonyl-3-t-butoxy-2-oxoazetidine-1yl)-α-(acetyl) acetamide i.e.

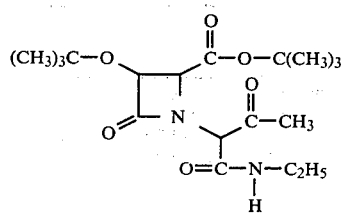

Erythro-β-t-butoxy-DL-aspartic acid α-t-butyl ester (750 mg, 3 millimole) dissolved in a mixture of chloroform (30 ml) and water (30 ml) was added to 40% aqueous pyruvaldehyde (0.56 ml 3 millimole) and ethylisonitrile (165 mg, 3 millimole) and was stirred under nitrogen at room temperature for 72 hours. After completion of the reaction, the chloroform phase of the reaction solution was combined with another chloroform phase obtained by extracting the aqueous phase twice using 20 ml portions of chloroform. The combined solutions were washed twice using 20 ml portions of a saturated solution of sodium chloride and the chloroform phase was then dried over Glauber's salt. The residue was transferred to a column (diameter about 3 cm) packed with 40 g of silica gel (Q23). Purification was effected by column chromatography using a solvent mixture of benzene and ethyl acetate (2:1 by volume). The eluate was divided into 3 ml fractions. Fractions 21 to 50 were collected and combined. The solvent was evaporated off under reduced pressure giving crystals (180 mg) having the following physical characteristics.

Melting point: 119°–120° C.

Elemental analysis as $C_{18}H_{30}N_2O_6$
(molecular weight 370.44)

|  | C | H | N |
|---|---|---|---|
| Calculated (%): | 58.36 | 8.16 | 7.56 |
| Observed (%): | 58.15 | 8.12 | 7.46 |

Infra-red absorption spectrum: $\gamma_{max}^{KBr}$ (cm$^{-1}$)
1790 (sh), 1780, 1720 1620 (br)

N.M.R. spectrum: δ CD₃OD—CDCl₃
Note: ( ) indicates the coupling
constant (Hz). 1.17 [t 3 H (8)] 1.30
(S 9 H) 1.53 (S 9H) 2.0 (S 2.6H) 2.33
(brs 0.4H) 3.30 [q 2H (8)] 4.0 [d 1H
(2)] 4.80 [d 1H (2)]
Thin layer chromatography:
Using a silica gel plate (Merck) and
benzene/ethyl acetate (1:1, by volume), a single
spot was observed (Rf = 0.74).

From these data, the crystals were identified as 3,4-erythro-ethyl-α-(4-t-butoxycarbonyl-3-t-butoxy-2-oxoazetidine-1-yl)-α-(acetyl) acetamide. This substance becomes brown when subjected to the FeCl₃ colour reaction on the thin layer chromatography plate, while the N.M.R. spectrum reveals a single peak (δ14.97) which is exchangeable with deuterated methanol.

These facts indicate the presence of this substance mainly in enol form.

EXAMPLE 8

Preparation of (4S)-ethyl-α-(4-methoxycarbonyl-2-oxoazetidine-1-yl)-α-(phenyl) acetamide, i.e.

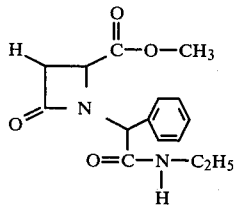

L-aspartic acid-α-methyl ester (4.41 g, 30 millimole) suspended in methanol (200 ml) was added to benzaldehyde (3.18 g, 30 millimole) and ethylisonitrile (1.82 g, 33 millimole). The mixture was stirred under nitrogen at room temperature for 48 hours. After completion of the reaction, the solvent was evaporated off under reduced pressure to given an oily substance which was then transferred to a column (diameter about 8 cm) packed with 600 g of silica gel (Q23) to effect purification by column chromatography. The eluate was divided into 12 ml fractions and fractions 1 to 72, 73 to 88 and 89 to 260 were eluted using solvent systems of hexane/ethyl acetate (1:2 by volume) hexane/ethyl acetate (1:3 by volume) and ethyl acetate/methanol (200:1 by volume) respectively. Fractions 71 to 221 were collected and combined and the solvent was removed by distillation to yield crystals (4.17 g) having the following physical characteristics [yield 47.9%].

| Elemental analysis as C₁₅H₁₈N₂O₄ (molecular weight 290.31): | | | |
|---|---|---|---|
| | C | H | N |
| Calculated (%): | 62.05 | 6.25 | 9.65 |
| Observed (%): | 61.77 | 6.38 | 9.37 |
| Infra-red absorption spectrum: $\gamma_{max}^{KBr}$ (cm⁻¹) 1740-1770, 1670, 1660 | | | |
| N.M.R. spectrum: δ CDCl₃ Note: ( ) indicates the coupling constant (Hz). 1.06 [t 1.35H (7)] 1.20 [t 1.65H (7)] 2.67-3.63 (m 4 H) 3.40 (S 1.65H) 3.73 (S 1.35H) 3.8-4.57 (m 1 H) 5.35 (S 1.65 H) 5.42 (S 1.35 H) 7.30, 7.35 (2S 5H) 6.4-7.9 (1H) | | | |
| Thin layer chromatography: Using a silica gel plate (Merck) and benzene/ethyl acetate (1:1, by volume), two spots were observed (Rf = 0.30 and Rf = 0.36). | | | |

EXAMPLE 9

Preparation of (4S)-phenyl-α-(4-benzyloxycarbonyl-2-oxoazetidine-1-yl)-α-(phenyl) acetamide, i.e.

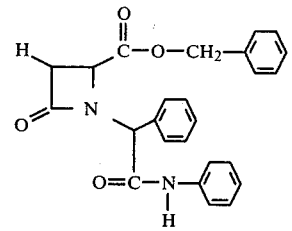

L-aspartic acid-α-benzyl ester (40 g 179.2 millimole) was suspended in methanol (1.3 liter) and was added to benzaldehyde (19 g, 179.2 millimole) and phenylisonitrile (19.4 g, 188.2 millimole). The mixture was stirred under nitrogen at room temperature for 64 hours. After the removal of the solvent by distillation under reduced pressure, the resulting oily substance was added to a saturated sodium chloride solution (500 ml) and ethyl acetate (500 ml) to effect extraction. The ethyl acetate layer was washed three times using a saturated sodium chloride solution and dried over Glauber's salt. After the removal of the solvent by distillation under reduced pressure, the resulting oily substance was transferred to a column (diameter about 8 cm) packed with 600 g of silica gel (C-200 obtainable from Wako Junyaku K. K. Japan), to effect purification by column chromatography using a solvent system of n-hexane/ethyl acetate (1:1, by volume). The eluate was divided into 18 ml fractions. Fractions 79 to 129 were collected and combined and the solvent was removed by distillation under reduced pressure to yield a glassy substance having the following physical characteristics.

| Elemental analysis as C₂₅H₂₂N₂O₄ (molecular weight 414.44): | | | |
|---|---|---|---|
| | C | H | N |
| Calculated (%): | 72.45 | 5.35 | 6.76 |
| Observed (%): | 72.57 | 5.50 | 6.57 |
| Infra-red absorption spectrum: $\gamma_{max}^{CHCl_3}$ (cm⁻¹) 1780 (sh), 1770, 1750 (sh), 1695, 1602 | | | |
| N.M.R. spectrum: δ CDCl₃ Note: ( ) indicates the coupling constant (Hz). 2.67-3.50 (m 2 H), 3.87, 4.53 [each t (4.0), dd (2.5, 5.5), 1H], 4.83, 5.15, 5.20 (each S 1H), 5.50, 5.57 (each S 1 H), 6.87-7.80 (m 15H) 8.73, 9.80 (each brs 1H) | | | |
| Mass spectrum: M⁺ +1 415; M⁺ 414, 294, 266, 204, 91 | | | |
| Thin layer chromatography: Using a silica gel plate (Merck) and n-hexane/ethyl acetate (1:1 by volume), a single spot was observed (Rf = 0.54). | | | |

From these data, the obtained glassy substance was identified as (4S)-phenyl-α-(4-benzyloxycarbonyl-2-oxoazetidine-1-yl)-α-(phenyl) acetamide [yield: 29.7%].

EXAMPLE 10

Preparation of (4S)-phenyl-α-(4-benzyloxycarbonyl-2-oxoazetidine-1-yl)-α-(3-methoxyphenyl) acetamide, i.e.

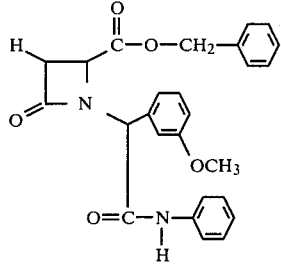

L-aspartic acid-α-benzyl ester (2.25 g, 10 millimole) was suspended in methanol (80 ml) and was added to m-anisaldehyde (1.36 g, 10 millimole) and phenylisonitrile (1.08 g, 10 millimole). The mixture was stirred under nitrogen at room temperature for 45 hours. An oily substance obtained by removing the solvent under reduced pressure, was transferred to a column (diameter about 5 cm) packed with C-200 silica gel (250 g). Purification was carried out by column chromatography using a solvent system of n-hexane/ethyl acetate (3:2, by volume). The eluate was divided into 15 ml fractions. Fractions 61 to 93 were collected and combined and the solvent was evaporated off under reduced pressure to give an oily substance (1.05 g) having the following physical characteristics.

| Elemental analysis as $C_{26}H_{24}N_2O_5$ (molecular weight 444.47): | | | |
|---|---|---|---|
| | C | H | N |
| Calculated (%): | 70.25 | 5.44 | 6.30 |
| Observed (%): | 70.33 | 5.75 | 6.19 |

Infra-red absorption spectrum: $\gamma_{max}^{CHCl_3}$ (cm$^{-1}$)
1780 (sh), 1770, 1750 (sh), 1695, 1602
N.M.R. spectrum: δ CDCl$_3$
Note: ( ) indicates the coupling constant (Hz). 2.73–3.50 (m 2H), 3.67, 3.70 (each S 3H), 3.90, 4.57 [each t (4.0), dd (2.5, 5.5), 1H], 4.87, 5.17, 5.20 (each S 2H), 5.47, 5.53 (each S 1H), 6.67–7.83 (m 14H), 8.70, 9.80 (each brs 1H)
Mass spectrum:
M+ 444, 324, 296, 234, 91
Thin layer chromatography:
Using a silica gel plate (Merck) and n-hexane/ethyl acetate (1:1, by volume), single spot was observed (Rf = 0.54).

From these data, the oily substance was identified as (4S)-phenyl-α-(4-benzyloxycarbonyl-2-oxoazetidine-1yl)-α-(3-methoxyphenyl)acetamide [yield: 23.6%]

EXAMPLE 11

Preparation of (4S)-phenyl-α-(4-benzyloxycarbonyl-2-oxoazetidine-1-yl)-α-(5-methylfuranyl-2-yl) acetamide, i.e.

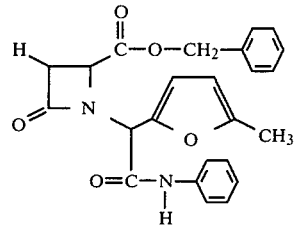

L-aspartic acid-α-benzyl ester (2.23 g, 10 millimole) suspended in methanol (80 ml) was added to 5-methylfurfural (1.1 g, 10 millimole) and phenylisonitrile (1.08 g, 10.5 millimole). The mixture was stirred at room temperature for 6 days. An oily substance was obtained by removing the solvent under reduced pressure. This substance was transferred to a column (diameter about 6 cm) packed with 350 g of silica gel (C-200) for purification. Elution is effected using a solvent system of n-hexane/ethyl acetate (3:2, by volume). The eluate was divided into 10 ml. fractions and fractions 80 to 129 were collected and combined and the solvent was evaporated off under reduced pressure to give an oily substance (558 mg) having the following physical characteristics.

| Elemental analysis as $C_{24}H_{22}N_2O_5$ (molecular weight 418.43) | | | |
|---|---|---|---|
| | C | H | N |
| Calculated (%): | 68.89 | 5.30 | 6.70 |
| Observed (%): | 69.22 | 5.41 | 6.55 |

Infra-red absorption spectrum: $\gamma_{max}^{CHCl_3}$ (cm$^{-1}$)
1780 (sh), 1770, 1740, 1700, 1603
N.M.R. spectrum: $\delta^{CDCl_3}$ Note: ( ) indicates the coupling constant (Hz).
2.10, 2.16 (each S, 3H), 2.77–3.53 (m, 2H), 3.97, 4.59 (each m, 1H), 4.97, 5.23 (each brs, 2H), 5.53, 5.57 (each S, 1H), 5.83 (m, 1H), 6.26 (m, 1H), 6.80–7.80 (m, 10H), 8.63, 9.97 (each brs, 1H)
Mass spectrum: (m/e)
M+ 418, 298, 270, 208, 91
Thin layer chromatography:
Using a silica gel plate (Merck) and n-hexane/ethyl acetate (1:1, by volume), two spots were observed (Rf = 0.58 and Rf = 0.61).

From these data, the oily substance was identified as (4S)-phenyl-α-(4-benzyloxy-carbonyl-2-oxoazetidine-1-yl)-α-(5-methylfuran-2-yl)acetamide [yield: 13.8%].

EXAMPLE 12

Preparation of (4S)-methyl-α-(4-benzyloxycarbonyl-2-oxoazetidine-1-yl)-α-(phenyl) acetate, i.e.

Quinoline (18 ml, 152.0 millimole) was added, under anhydrous condition at a temperature of 0° C., to anhydrous chloroform (340 ml) containing phosphorus pentachloride (15.83 g, 76.0 millimole), and the solution was added, at 0° C. over 20 minutes, to (4S)-phenyl-α-(4-benzyloxycarbonyl-2-oxoazetidine-1-yl)-α-(phenyl)- acetamide (21.0 g, 50.7 millimole) consisting of a diastereomeric mixture (ratio of about 1:1), prepared as in Example 9 and dissolved in anhydrous chloroform (80 ml). The reaction mixture was stirred at from 0° to 5° C. for 3 hours. The solution was added to anhydrous methanol (300 ml) at 0° C. and stirred at room temperature for 3 hours. After this, the solution was added at 0° C. to 1 N HCl (400 ml) and methanol (300 ml), followed by stirring at room temperature for 1 hour. About 60% of the solution was removed by distillation under reduced pressure. The remaining solution was extracted using three 250 ml portions of ethyl acetate, the ethyl accetate phase was washed three times using a saturated solution of sodium chloride and the organic phase was dried over Glauber's salt. By removing the solvent under reduced pressure, an oily substance was obtained, which was transferred to a column (diameter about 8 cm) packed with C-200 silica gel (650 g). In order to purify it by column chromatography, a mixture of hexane/ethyl acetate (1.4 liter, 5:2, by volume) was passed through the column, followed by elution using a solvent mixture of hexane/ethyl acetate (3:2, by volume). The eluate was divided into 15 ml fractions. Fractions 63 to 104 was collected and combined and the solvent was evaporated off under reduced pressure to give an oily substance (7.9 g, yield 44.4%). The oily substance obtained from Fractions 74 to 104 has the following physical characteristics.

| N.M.R. spectrum: $\delta^{CDCl_3}$ [the coupling constant (Hz) is indicated in ( )] |
|---|
| 2.83 [dd, 0.5H (2.5, 14.0)], 3.07 [d, 1H (4.0)], 3.12 [dd, 0.5H (5.5, 14.0)], 3.60 (S, 1.5H), 3,70 (S, 1.5H), 4.23 [t, 0.5H(4.0)], 4.42 [dd, 0.5H (2.5, 5.5)], 4.70 (brs, 1H), 5.20 (S, 1H), 5.50 (S, 1H), 7.20–7.40 (m, 10H) |
| Infra-red absorption spectrum: $\gamma_{max}^{CHCl_3}$ (cm$^{-1}$) 1780 (sh), 1775, 1750, 1740 (sh) |
| Mass spectrum: (m/e) M$^+$ 353, 294, 266, 91 |
| Thin layer chromatography: Using a silica gel plate (Merck) and hexane/ ethyl acetate (1:1, by volume), two spots were observed (Rf = 0.52 and Rf = 0.61). |

From these data, the oily substance obtained was identified as (4S)-methyl-α-(4-benzyloxycarbonyl-2-oxoazetidine-1-yl)-α-(phenyl) acetate consisting of a diastereomeric mixture of two compounds in a ratio of about 1:1.

EXAMPLE 13

Preparation of (4S)-methyl-α-(4-benzyloxycarbonyl-2-oxoazetidine-1-yl)-α-(3-methoxyphenyl) acetate, i.e.

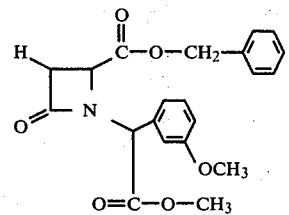

Quinoline (0.825 ml, 6.96 millimole) was added, under anhydrous condition at a temperature of 0° C., to anhydrous chloroform (15.4 ml) containing phosphrus pentachloride (725 mg, 3.48 millimole) and was then added, at 0° C. over 10 minutes, to anhydrous chloroform (6 ml) containing (4S)-phenyl-α-(4-benzyloxycarbonyl-2-oxoazetidine-1-yl)-α-(3-methoxyphenyl) acetamide (1.03 g, 2.32 millimole), in Example 10. The reaction mixture was stirred for 3½ hours at 0° C. and was then added to anhydrous methaol (14 ml) at 0° C. After stirring at room temperature for 3 hours, the solution was added to 1 N HCl (18 ml) and methanol (18 ml) at 0° C. and was stirred at room temperature for 1 hour. About 60% of the solvent was removed by distillation under reduced pressure and the remaining solution was extracted using three 30 ml portions of ethyl acetate. The organic phase was washed three times using a saturated solution of sodium chloride and was dried over Glauber's salt. By removing the solvent under reduced pressure, an oily substance was obtained which was transferred to a column (diameter about 4 cm) packed with C-200 silica gel (120 g) and was purified by column chromatography using a solvent system of hexane/ethyl acetate (3:2, by volume). The eluate was divided into 6 ml fractions. Fractions 56 to 82 were collected and combined and the solvent was removed by evaporation under reduced pressure to give an oily substance (473 mg) in a yield of 53.2%. The oily substance obtained from fractions 66 to 82 has the following physical characteristics.

| N.M.R. spectrum: $\delta^{CDCl_3}$ [The coupling constant (Hz) is indicated in ( ).] |
|---|
| 2.85 [dd, ⅔ H (2.5, 15.0)], 3.07 [d, ⅔ H (4.0)], 3.27 [dd, ⅔ H(5.5, 15.0)], 3.63 (S, 1H), 3.40 (S, 5H), 4.23 [t, ⅓ H(4.0)], 4.45 [dd, ⅔ H (2.5, 5.5)], 4.72, 4.74 (AB doublet, 4/3 H), 5.20 (S, ⅔H), 5.48 (brs, 1H), 6.70–7.40 (m, 9H) |
| Infra-red absorption spectrum: $\gamma_{max}^{CHCl_3}$ (cm$^{-1}$) 1780 (sh), 1770, 1750, 1740 (sh), 1600, 1590 |
| Mass spectrum: (m/e) M$^+$ 383, M+1:384, 324, 296, 91 |
| Thin layer chromatography: Using a silica gel plate (Merck) and hexane/ethyl acetate (1:1, by volume), two spots (Rf = 0.47 and Rf = 0.51) were observed, which suggested a ratio of about 2:1. |

From these data, the oily substance was identified as (4S)-methyl-α-(4-benzyloxycarbonyl-2-oxoazetidine-1-yl)-α-(3-methoxyphenyl) acetate consisting of a diastereomeric mixture of two compounds in a ratio of about 2:1. Similarly, an oily substance obtained from fractions 56 to 82 was identified as a diastereomeric mixture of two compounds in a ratio of about 1:1.

EXAMPLE 14

Preparation of (4S)-methyl-α-(4-benzyloxycarbonyl-2-oxoazetidine-1-yl)-α-(5-methylfuran-2-yl) acetate, i.e.

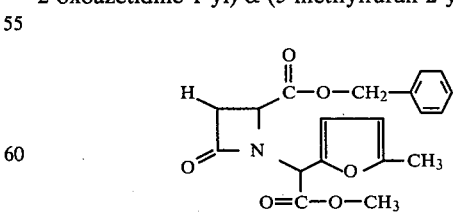

Quinoline (0.46 ml, 3.87 millimole) was added, under anhydrous conditions at 0° C., to anhydrous chloroform (8.6 ml) containing phosphorus pentachloride (403 mg, 1.94 millimole) and was then added over 10 minutes, to anhydrous chloroform (6 ml) containing (4-S)-phenyl- α-(4-benzyloxycarbonyl-2-oxoazetidine-1-yl)-α-(5-methylfuran-2-yl) acetamide (540 ml, 1.29 millimole) prepared as in Example 11. The solution was stirred at 0° C. for 3½ hours and was then added to methanol, followed by stirring at room temperature for 1 hour. About 60% of the solvent was evaporated off under reduced pressure and the remaining solution was extracted using three 30 ml portions of ethyl acetate. The organic phase was washed three times using a saturated solution of sodium chloride and was dried over Glauber's salt.

The solvent was removed under reduced pressure to give an oily substance which was then transferred to a column (diameter about 3 cm) packed with 60 g of C-200 silica gel. The substance was purified by column chromatography using a solvent system of hexane/ethyl acetate. The eluate was divided into 3 ml fractions and fractions 55 to 72 were collected and combined and the solvent was evaporated off under reduced pressure to give an oily substance (191 mg) in a yield of 41.4%. An oily substance obtained from fractions 60 to 65 has the following physical characteristics.

N.M.R. spectrum: δ CDCl3
  Note: ( ) indicates the coupling constant (Hz).
  2.17 (S, 1.8H), 2.23 (S, 1.2H), 2.87 [dd, 0.6H (2.5, 14.5)], 3.10 [d, 0.8H (4.0)] 3.30 [dd, 0.6H (5.0, 14.5)], 3.65 (S, 1.2H), 3.73 (S, 1.8H), 4.18 [t, 0.4H (4.0)], 4.53 [dd, 0.6H (2.5, 5.0)], 4.90, 4.93 (AB doublet, 1.2H), 5.20, (S, 0.8H), 5.57 (S, 1H), 5.87 (m, 1H), 6.17 [d, 0.6H (3.0)], 6.23 [d, 0.4H (3.0)], 7.30 (S, 2H), 7.37 (S, 3H)
Infra-red absorption spectrum: $\gamma_{max}^{CHCl_3}$ (cm$^{-1}$)
  1780 (sh), 1770, 1755, 1740 (sh)
Mass spectrum: (m/e)
  M+ 357, 329, 298, 270, 91
Thin layer chromatography:
Using a silica gel plate (Merck) and benzene/ethyl acetate (1:1, by volume), a single spot was observed (Rf = 0.49).

From these data, the oily substance was identified as (4S)-methyl-α-(4-benzyloxycarbonyl-2-oxoazetidine-1-yl)-α-(5-methylfuran-2-yl) acetate consisting of two diastereomeric isomers in a ratio of about 2:3.

Similarly, an oily substance obtained from fractions 52 to 72 was identified as a diastereomeric mixture of two compounds in a ratio of about 2:3.

EXAMPLE 15

Preparation of (4S)-methyl-α-(4-carboxyl-2-oxoazetidine-1-yl)-α-(phenyl) acetate, i.e.

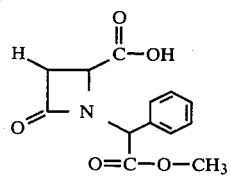

(4S)-methyl-α-(4-benzyloxycarbonyl-2-oxoazetidine-1-yl)-α-(phenyl) acetate (4.0 g, 11.3 millimole) consisting of a diastereomeric mixture (ratio about 1:1) prepared as in Example 12, was dissolved in dioxane (250 ml), to which was added 10% palladium/carbon catalyst (1.0 g). The solution was stirred at room temperature under atmospheric pressure for 17 hours while nitrogen was passed through the solution. The catalyst was removed and the solvent was evaporated off under reduced pressure to give an oily substance (2.89 g) having the following physical characteristics.

N.M.R. spectrum: δ CHCl3 [The coupling constant (Hz) is indicated in ( ).]
  2.70-3.50 (m, 2H), 3.70, 373 (each S, 5H 4.07-4.50 (m, 1H), 5.47, 5.53 (each S, 1H), 7.30, 7.33 (each S, 5 H)
Infra-red absorption spectrum: $\gamma_{max}^{CHCl_3}$ (cm$^{-1}$)
  1780 (sh), 1775, 1755, 1740 (sh), 1730 (sh), 1710 (sh)
Thin layer chromatography:
Using a silica gel plate (Merck) and benzene/ethyl acetate/acetic acid (6:2:1, by volume), a single spot was observed (Rf = 0.32).

From these data, the oily substances was identified as (4S)-methyl-α-(4-carboxyl-2-oxoazetidine-1-yl)-α-(phenyl) acetate consisting of a diastereomeric mixture of two compounds in a ratio of about 1:1 (yield: 97.0%).

EXAMPLE 16

Preparation of (4S)-methyl-α-(4-carboxyl-2-oxoazetidine-1-yl)α-(3-methoxyphenyl) acetate,

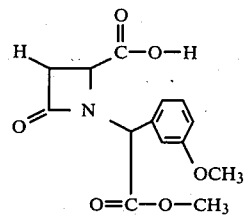

(4S)-methyl-60 -(4-benzyloxycarbonyl-2-oxoazetidine-1-yl)-α-(3-methoxyphenyl) acetate (470 mg, 1.23 millimole) consisting of a diastereomeric mixture (ratio about 1:1), prepared as in Example 13, was dissolved in dioxane (25 ml), to which 10% palladium/carbon catalyst (100 mg) was added. The mixture was stirred at room temperature under atmospheric pressure for 14 hours, while nitrogen was passed through the solution. The catalyst was removed from the reaction mixture and the solvent was removed under reduced pressure to give an oily substance (354 mg) having the following physical characteristics.

N.M.R. spectrum: δ CHCl3 [The coupling constant (Hz) is indicated in ( ).]
  2.73-3.50 (m 2H), 3.70-3.80 (m, 6H), 4.13-4.50 (m, 1H), 5.47 (S, 0.5H), 5.53 (S, 0.5H), 6.75-7.47 (m, 4H)
Infra-red absorption spectrum: $\gamma_{max}^{CHCl_3}$ (cm$^{-1}$)
  1780 (sh), 1770, 1750, 1740 (sh), 1730 (sh), 1710 (sh), 1600, 1590
Thin layer chromatography:
Using a silica gel plate (Merck) and benzene/ethyl acetate/acetic acid (6:2:1, by volume), a single spot was observed (Rf = 0.26).

From these data, the oily substance was identified as (4S)-methyl-α-(4-carboxyl-2-oxoazetidine-1-yl)-α-(3-methoxyphenyl) acetate consisting of a diastereomeric mixture of two compounds (ratio about 1:1) [yield 98.0%].

EXAMPLE 17

Preparation of (4S)-methyl-α-(4-carboxyl-2-oxoazetidine-1-yl)-α-(5-methylfuran-2-yl) acetate, i.e.

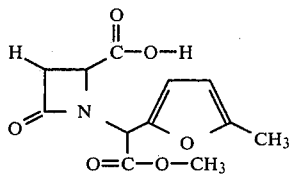

(4S)-methyl-α-(4-benzyloxycarbonyl-2-oxazetidine-1-yl)-α-(5-methylfuran-2-yl) acetate (180 mg, 0.5 millimole) consisting of a diastereomeric mixture (ratio about 2:3), prepared as in Example 14, was dissolved in dioxane (12.5 ml). To the mixture was added 10% palladium/carbon catalyst (50 ml). Nitrogen was passed through the solution for 14 hours, while it was stirred at room temperature under atmospheric pressure. After removal of the catalyst, the solvent was evaporated off under reduced pressure to give an oily substance (130 mg) having the following physical characteristics.

N.M.R. spectrum: δ CDCl$_3$
Note: ( ) indicates the coupling constant (Hz).
2.22 (S, 1.8H), 2.27 (S, 1.2H), 2.77–3.57 (m, 2H), 3.77 (S, 3H), 4.07–4.63 (m, 1H), 5.60 (brs, 1H), 5.93 (m, 1H), 6.25 [d, 0.6H (3.0)], 6.32 [d, 0.4H (3.0)]

Infra-red absorption spectrum: $\gamma_{max}^{CHCl_3}$ (cm$^{-1}$)
1780 (sh), 1770, 1755, 1740 (sh), 1730 (sh), 1710

Thin layer chromatography:
Using a silica gel plate and benzene/ethyl acetate/acetic acid (6:2:1, by volume), a single spot was observed (Rf = 0.27).

From these data, the oily substance was identified as (4S)-methyl-α-(4-carboxyl-2-oxoazetidine-1-yl)-α-(5-methylfuran-2-yl) acetate consisting of a mixture of two compounds in a ratio of about 2:3 [yield 97.0%].

What is claimed is:

1. A 2-azetidinone derivative selected from the group consisting of compounds of formulae (Ia) and (I'a) as follows, and their pharmaceutically acceptable salts:

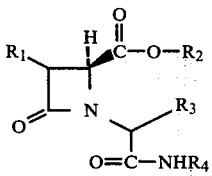

formula (Ia)

wherein:
R$_1$ is selected from the group consisting of aralkoxy, C$_1$5 alkanoyloxy, methanesulphonyloxy and p-toluenesulphonyloxy, any one of which groups may be mono-substituted with halogen, C$_1$ to C$_5$ alkyl, C$_1$ to C$_5$ alkoxy and nitro group; hydrogen, hydroxy, and C$_1$ to C$_5$ alkoxy group;

R$_2$ is selected from the group consisting of C$_1$ to C$_5$ alkyl and aralkyl, either of which groups may be mono-substituted with halogen, C$_1$ to C$_5$ alkyl, C$_1$ to C$_5$ alkoxy and nitro group; and hydrogen;

R$_3$ is selected from the group consisting of C$_1$ to C$_5$ alkyl, phenyl, naphtyl, aralkyl, C$_2$ to C$_5$ alkynyl, aralkynyl, C$_2$ to C$_5$ alkynyl, aralkynyl and acetyl, propionyl, and butyryl, and of which groupds may be mono-substituted with halogen, C$_1$ to C$_5$, alkyl, C$_1$ to C$_5$ alkoxy, C$_1$5 alkanoyloxy, hydroxy, amino, phthalylimino, carbobenzoxyamino benzylamino and nitro group; 2- or 3-furyl, 5-methyl-2-furyl, 2- or 3-thienyl, 2- or 3-pyrrolyl, 2- or 4-imidazolyl, 3-pyrazolyl, 4-isoxazolyl, 2-, 3-, 4-, 5-, 6- or 7-indolyl or 2- or 3-benzo(b) furanyl; and R$_4$ is selected from the group consisting of C$_1$ to C$_5$ alkyl, C$_2$ to C$_5$ alkenyl, phenyl, naphthyl and aralkyl, any one of which groups may be mono-substituted with halogen, C$_1$ to C$_5$ alkyl, C$_1$ to C$_5$ alkoxy, C$_1$5 alkanoyloxy, hydroxy, amino, phthalylimino, carbobenzoxyamino, benzylamino, and nitro group,

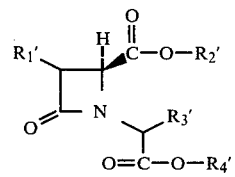

formula (I'a)

wherein:
R'$_1$ is selected from the group consisting of aralkoxy, C$_1$5 alkanoyloxy, methanesulphonyloxy and p-toluene-sulphonyloxy, any one of which groups may be mono-substituted with halogen, C$_1$ to C$_5$ alkyl, C$_1$ to C$_5$ alkoxy, and nitro; hydrogen, hydroxy, and C$_1$ to C$_5$ alkoxy group;

R'$_2$ is selected from the group consisting of C$_1$ to C$_5$ alkyl, aralkyl and t-butyl dimethylsilyl and trimethylsilyl, and one of which groups may be mono-substituted with halogen, C$_1$ to C$_5$ alkyl, C$_1$ to C$_5$ alkoxy and nitro group; and hydrogen;

R'$_3$ is selected from the group consisting of C$_1$ to C$_5$ alkyl, phenyl, naphthyl, aralkyl, C$_2$ to C$_5$ alkenyl, aralkynyl, C$_2$ to C$_5$ alkynyl, aralkenyl, acetyl, propionyl and butyryl, any one of which groups may be mono-substituted with halogen, C$_1$ to C$_5$ alkyl, C$_1$ to C$_5$ alkoxy, C$_1$5 alkanoyloxy, hydroxy, amino, phthalylimino, carbobenzoxyamino, benzylamino, and nitro group, 2- or 3-furyl, 2- or 3-thienyl, 2- or 3-pyrrolyl, 2- or 4-imidazolyl, 3-pyrazolyl, 4-isoxazolyl, 2-, 3-, 4-, 5-, 6- or 7-indolyl or 2- or 3-benzo(b)furanyl; and R'$_4$ selected from the group consisting of C$_1$ to C$_5$ alkyl, arallkyl and trialkylsilyl, any one of which groups may be mono-substituted with halogen, C$_1$ to C$_5$ alkyl, C$_1$ to C$_5$ alkoxy and nitro group, and hydrogen.

2. The compound of formula (Ia) of claim 1 wherein:
R$_1$ is selected from the group consisting of benzyloxy, C$_1$5 alkanoyloxy, p-toluenesulphyonyloxy and methanesulphonyloxy, any one of which groups may be monosubstituted with halogen, C$_1$ to C$_5$ alkyl, C$_1$ to C$_5$ alkoxy and nitro group; hydrogen, hydroxy and t-butoxy group;

R$_2$ is selected from the group consisting of C$_1$ to C$_5$ alkyl benzyl and diphenylmethyl, any of which groups may be mono-substituted with halogen, C$_1$ to C$_5$ alkyl, C$_1$ to C$_5$ alkoxy and nitro group; and hydrogen;

R$_3$ is selected from the group consisting of C$_1$ to C$_5$ alkyl, phenyl, naphthyl, benzyl, C$_2$ to C$_5$ alkenyl, styryl, cinnamyl, $C_2$ to $C_5$ alkynyl, 2-phenyl-1-ethynyl, acetyl, propionyl and butyryl, any one of which groups may be mono-substituted with halogen, $C_1$ to $C_5$ alkyl, $C_1$ to $C_5$ alkoxy, $C_15$ alkanoyloxy, hydroxy, amino, phthylimino, carbobenzoxyamino, benzylamino and nitro group; 2- or 3-furyl, 5-methyl-2-furyl, 2- or 3-thienyl, 2- or 3-pyrrolyl, 2- or 4-imidazolyl, 3-pyrazolyl, 4-isoxazolyl, 2-, 3-, 4-, 5-, 6- or 7-indolyl or 2- or 3-benzo(b)furanyl; and $R_4$ is selected from the group consisting of $C_1$ to $C_5$ alkyl, $C_2$ to $C_5$ alkenyl, phenyl, naphthyl, benzyl, diphenylmethyl, trityl and phthalidyl, and one of which groups may be monosubstituted with halogen, $C_1$ to $C_5$ alkyl, $C_1$ to $C_5$ alkoxy, $C_15$ alkanoyloxy, hydroxy, amino, phthalylimino, carbobenzoxyamino, benzylamino and nitro group.

3. The compound of claim 2, wherein $R_1$ is selected from the group consisting of hydrogen and t-butoxy group; $R_2$ is selected from the group consisting of methyl, t-butyl and benzyl group; $R_3$ is selected from the group consisting of i-propyl, phenyl, 3-methoxyphenyl, styryl, acetyl and 5-methyl-2-furyl group; and $R_4$ is selected from the group consisting of ethyl, t-butyl and phenyl group.

4. The compound of formula (I'a) of claim 1 wherein;
$R_1'$ is selected from the group consisting of benzyloxy, $C_15$ alkanoyloxy, p-toluenesulphonyloxy, and methanesulphonyloxy, any one of which groups may be monosubstituted with halogen, $C_1$ to $C_5$ alkyl, $C_1$ to $C_5$ alkoxy and nitro group; benzylamino, hydrogen, hydroxy and t-butoxy;
$R_2'$ is selected from the group consisting of $C_1$ to $C_5$ alkyl, benzyl, diphenylmethyl, trityl, phthalidyl and t-butyldimethylsilyl and trimethylsilyl, any one of which groups may be substituted with halogen, $C_1$ to $C_5$ alkyl, $C_1$ to $C_5$ alkoxy and nitro group; and hydrogen;
$R_3'$ is selected from the group consisting of $C_1$ to $C_5$ alkyl, phenyl, naphthyl, benzyl, $C_2$ to $C_5$ alkenyl, styryl, cinnamyl, $C_2$ to $C_5$ alkynyl, 2-phenyl-1-ethynyl, acetyl, propionyl, butyryl, 2- or 3-furyl, 2- or 3-thienyl, 2- or 3-pyrrolyl, 2- or 4-imidazolyl, 3-pyrazolyl, 4-isoxazolyl, 2-, 3-, 4-, 5-, 6- or 7-indolyl 5-methyl-2-furyl and 2- or 3-benzy(b)furanyl, any of which groups may be mono-substituted with halogen, $C_1$ to $C_5$ alkyl, $C_1$ to $C_5$ alkoxy, $C_15$ alkanoyloxy, amino, phthalylimino, carbobenzoxyamino, benzylamino and nitro group; and $R_4'$ is selected from the group consisting of $C_1$ to $C_5$ alkyl, benzyl, diphenylmethyl, trityl, phthalidyl, and t-butyldimethylsilyl and trimethylsilyl, and of which groups may be mono-substituted with halogen $C_1$ to $C_5$ alkyl, $C_1$ to $C_5$ alkoxy and nitro group; and hydrogen.

5. The compound of claim 4, wherein $R_1'$ is hydrogen; $R_2'$ is selected from the group consisting of benzyl group and hydrogen; $R_3'$ is selected from the group consisting of phenyl, 3-methoxyphenyl and 5-methyl-2-furyl group; and $R_4'$ is methyl group.

6. (4S)-t-butyl-α-(4-benzyloxycarbonyl-2-oxoazetidine-1-yl)-α-(acetyl) acetaminde.

7. (4S)-t-butyl-α-(4-methoxycarbonyl-2-oxoazetidine-1-yl)-α-(styryl) acetamide.

8. (4S)-t-butyl-α-(4-methoxycarbonyl-2-oxoazetidine-1-yl)-α-(isopropyl) acetamide.

9. (4S)-t-butyl-α-(4-benzyloxycarbonyl-2-oxoazetidine-1-yl)-α-(phenyl) acetamide.

10. (4S)-ethyl-α-(4-methoxycarbonyl-2-oxoazetidine-1-yl)-α-(acetyl) acetamide.

11. (4S)-ethyl-α-(4-benzyloxycarbonyl-2-oxoazetidine-1-yl)-α-(acetyl) acetamide.

12. 3,4-erythro-ethyl-α-(4-t-butoxycarbonyl-3-t-butoxy-2-oxoazetidine-1-yl)-α-(acetyl) acetamide.

13. (4S)-ethyl-α-(4-methoxycarbonyl-2-oxoazetidine-1-yl)-α-(phenyl) acetamide.

14. (4S)-phenyl-α-(4-benzyloxycarbonyl-2-oxoazetidine-1-yl)-α-(phenyl) acetamide.

15. (4S)-phenyl-α-(4-benzyloxycarbonyl-2-oxoazetidine-1-yl)-α-(3-methoxyphenol) acetamide.

16. (4S)-phenyl-α-(4-benzyloxycarbonyl-2-oxoazetidine-1-yl)-α-(5-methylfuran-2-yl) acetamide.

17. (4S)-methyl-α-(4-benzyloxycarbonyl-2-oxoazetidine-1-yl)-α-(phenyl) acetate.

18. (4S)-methyl-α-(4-benzyloxycarbonyl-2-oxoazetidine-1-yl)-α-(3-methoxyphenyl) acetate.

19. (4S)-methyl-α-(4-benzyloxycarbonyl-2-oxoazetidine-1-yl)-α-(5-methylfuran-2-yl) acetate.

20. (4S)-methyl-α-(4-carbonyl-2-oxoazetidine-1-yl)-α-(phenyl) acetate.

21. (4S)-methyl-α-(4-carboxyl-2-oxoazetidine-1-yl)-α-(3-methoxyphenyl) acetate.

22. (4S)-methyl-α-(4-carboxyl-2-oxoazetidine-1-yl)-α-(5-methylfuran-2-yl) acetate.

* * * * *